United States Patent [19]

Rensi

[11] Patent Number: 4,795,830

[45] Date of Patent: * Jan. 3, 1989

[54] USE OF WATER TO INHIBIT DECOMPOSITION OF MONOALKYLFORMAMIDES

[75] Inventor: Terence A. Rensi, Hockessin, Del.

[73] Assignee: E. I. Du Pont de Nemours and Company, Wilmington, Del.

[*] Notice: The portion of the term of this patent subsequent to Jul. 28, 2004 has been disclaimed.

[21] Appl. No.: 902,599

[22] Filed: Sep. 2, 1986

[51] Int. Cl.$^4$ .............................................. C07C 85/26
[52] U.S. Cl. ......................................................... 564/4
[58] Field of Search ............................. 560/338; 564/4

[56] References Cited

U.S. PATENT DOCUMENTS 4,207,251  6/1980  Heyboer ............................. 260/453
4,683,329  7/1987  Rao .................................... 560/338

Primary Examiner—Alan Siegel

[57] ABSTRACT

Elevated-temperature decomposition of monoalkylformamides to monoalkylamines and carbon monoxide is inhibited in the presence of small amounts of water.

18 Claims, No Drawings

USE OF WATER TO INHIBIT DECOMPOSITION OF MONOALKYLFORMAMIDES

BACKGROUND OF THE INVENTION

This invention concerns a process to inhibit the thermal decomposition of N-alkylformamides by adding thereto a small amount of water.

The N-alkylformamides of interest in the method of this invention are known compounds whose numerous uses are reported throughout the literature. For example, they are employed as reactants to produce isocyanate intermediates for pesticides. Oxidative dehydrogenation of formamides to form the corresponding isocyanates is disclosed in U.S. Pat. Nos. 4,207,251 and 537,726. The processes described in those patents and other processes dependent on high temperature reactions involving N-alkylformamides will be improved by the method described herein for inhibiting their premature decomposition. Control of the decomposition problem brings attendant benefits of improved product yields, minimization of byproduct formation, and the like.

SUMMARY OF THE INVENTION

This invention concerns a method for inhibiting the thermal decomposition of N-alkylformamid(s) to corresponding N-alkylamine(s) and carbon monoxide, comprising contacting the N-alkylformamide(s) with water in an amount of about 0.1 to 5% by weight of the formamide(s). Preferred amounts of water are about 0.5 to 1.5% by weight of the formamide(s). In reactions involving vaporization of the formamide preparatory to contact with other reactants, it is preferred that the water and formamide be mixed prior to vaporization.

This invention concerns an improvement in any reaction in which N-alkylformamides are exposed to elevated temperature. The benefits of this invention are most evident at reaction temperatures above about 200° C., and at pressures of about 1 to 10 atmospheres. Significant improvements can be seen, however, at temperatures as low as about 180° C. The N-alkylformamides of concern in the process of this invention are straight and branched chain lower alkyls, preferably $C_1$ to $C_4$, and most preferably monomethylformamide (MMF).

DETAILS OF THE INVENTION

Continuous Vaporizer Procedure

Following are experimental details concerning vaporization studies that show, in Tables 1 and 2, the benefits of this invention. A 1" o.d. cylinder of stainless steel was fitted with a quartz sightglass (so inside volume of liquid could be determined), an inlet tube for liquid MMF, a pressure gauge, an internal thermocouple (submerged), and an outlet tube for MMF vapor. The assembly was inserted into a potentiometrically-controlled electric furnace and carefully insulated. The vapor outlet tube was connected to a pressure-regulating valve and the effluent gases passed sequentially to a condenser (approximately 20° C.), a trap containing 1N HCl, and a bubble flow meter. In a typical experiment, liquid MMF was metered into the cylinder until approximately 50% of the target level was reached and the heater energized while maintaining MMF flow. As the inside temperature passed 185° C., the pressure controller was adjusted to raise internal temperature to the target valve. The electric furnace was then adjusted until the target MMF level was reached. The system was allowed to equilibrate for 2 to 4 hours before data collection began. Evolution of the carbon monoxide (CO) was measured at the bubble flow meter and identity of the gas verified by GC on a molecular sieve column. The MMF collected at the condenser was titrated as a 20% aqueous solution with standardized acid, and the acid trap contents titrated with standardized NaOH to measure total monomethylamine (MMA). The decomposition measured by CO evolution and MMA titration generally agreed within 1% so only CO evolution was measured in certain of the later experiments. Examination of condensed MMF by GC revealed one small peak (<0.5 area %) aside from MMA and MMF.

Table 1 records typical vaporization data relative to monomethylformamide in the absence of water. It can be seen from this Table that the amount of decomposition is dependent on residence time and temperature.

TABLE 1

MMF Decomposition Results Without Water Addition

| Run | Temperature (°C.) | Residence Time (Min) | Decomposition (%) |
|---|---|---|---|
| A | 231 | 96 | 13.3 |
| B | 228 | 15 | 1.8 |
| C | 222 | 93 | 8.1 |
| D | 217 | 46 | 4.2 |
| E | 213 | 89 | 6.5 |
| F | 210 | 46 | 3.9 |
| G | 205 | 93 | 3.9 |

EXAMPLES 1 to 3

This invention produces particularly notable results at relatively high temperatures and/or high residence times; see Table 2, Example 2 vs. Run D and Example 3 vs. Runs C and A. Nevertheless, significant improvements are also produced at more moderate conditions of temperature and residence time; see Example 1 vs. Run F. The Table depicts lowered decomposition rates of 30% to more than 60% overall.

TABLE 2

Conditions and Results for Continuous Vaporizer

| Run or Ex. No. | Temperature (°C.) | Water (%) | Residence Time (Min) | Decomposition (%) |
|---|---|---|---|---|
| F | 210 | None | 46 | 3.9 |
| 1 | 212 | 1 | 50 | 2.5 |
| D | 217 | None | 46 | 4.2 |
| 2 | 220 | 1 | 48 | 3.1 |
| C | 222 | None | 91 | 7.8 |
| A | 231 | None | 96 | 13.3 |
| 3 | 235 | 1 | 88 | 4.4 |

Refluxing Batch Procedure

The apparatus consisted of a 500-ml round bottom flask equipped with a heating mantle, watercooled reflx condenser, and thermometer. The tests were done by charging about 300 g of MMF to the flask and heating to a boil. After boiling was established, the condenser vent was connected to a trap cooled with dry ice/acetone. The vent was disconnected from the trap after about 2½ hours, and the amount of MMA collected was weighed. From this test, the amount of MMA evolved per g MMF per hour was calculated.

EXAMPLES 4 to 6

Results of batch-type tests are presented in Table 3 in which water was added to determine the effect on decomposition rate. At an initial concentration of about 1%, water effectively stopped MMA elution when present initially or when added after the MMF had been boiling for several hours. With 1% water present initially, no MMA was being generated even after one day. When about 0.3% water was added initially, MMA evolution occurred but at a lower rate than would be expected with no water added.

TABLE 3

| | CONDITIONS AND RESULTS FOR BATCH-TYPE BOILING WITH WATER | | | |
|---|---|---|---|---|
| | | | Decomposition Rate | |
| Ex. No. | Conditions | Temp °C. | g MMA/ (g MMF) (hr) | % MMF/hr |
| 4 | 1% water added | | | |
| | Initial | 190 | 0 | 0 |
| | +1 day | 190 | 0 | 0 |
| 5 | 1% water added after initial MMA rate check | | | |
| | Initial (no water) | 195 | $3.2 \times 10^{-3}$ | 0.6 |
| | After water added | 190 | 0 | 0 |
| 6 | 0.3% water added Initial | 195 | $1.5 \times 10^{-3}$ | 0.3 |

The embodiments of the invention in which an exclusive property or privilege is claimed are defined as follows:

1. A method for inhibiting thermal decomposition, during heating, to a temperature of 180° C. or above N-alkylformamide to the corresponding N-alkylamines and carbon monoxide, comprising contacting the N-alkylformamide with water in an amount up to about 5 percent by weight of the formamide.

2. A method according to claim 1 comprising contacting the N-alkylformamide with water in an amount of 0.5 to 1.5 percent by weight of the formamide.

3. A method according to claim 1 wherein the alkylformamide is a $C_1$ to $C_4$ alkylformamide.

4. A method according to claim 3 wherein the alkylformamide is monomethylformamide.

5. A method according to claim 2 wherein the alkylformamide is a $C_1$ to $C_4$ alkylformamide.

6. A method according to claim 5 wherein the alkylformamide is monomethylformamide.

7. A method according to claim 1 comprising vaporization of the alkylformamide preparatory to contact with other reactants.

8. A method according to claim 7 wherein the alkylformamide is a $C_1$ to $C_4$ alkylformamide.

9. A method according to claim 8 wherein the alkylformamide is monomethylformamide.

10. A method according to claim 2 comprising vaporization of the alkylformamide preparatory to contact with other reactants.

11. A method according to claim 10 wherein the alkylformamide is a $C_1$ to $C_4$ alkylformamide.

12. A method according to claim 11 wherein the alkylformamide is monomethylformamide.

13. A method according to claim 7 wherein the water and formamide are mixed prior to vaporization.

14. A method according to claim 13 wherein the alkylformamide is a $C_1$ to $C_4$ alkylformamide.

15. A method according to claim 14 wherein the alkylformamide is monomethylformamide.

16. A method according to claim 2 wherein the water and formamide are mixed prior to vaporization.

17. A method according to claim 16 wherein the alkylformamide is a $C_1$ to $C_4$ alkylformamide.

18. A method according to claim 17 wherein the alkylformamide is monomethylformamide.

* * * * *

UNITED STATES PATENT AND TRADEMARK OFFICE
CERTIFICATE OF CORRECTION

PATENT NO. : 4,795,830

DATED : January 3, 1989

INVENTOR(S) : Terence Andrew Rensi

It is certified that error appears in the above-identified patent and that said Letters Patent is hereby corrected as shown below:

Column 3, line 34, insert --of an-- after the phrase, "or above". Delete "," after the word, "heating".

Column 3, line 37, insert --from about 0.1-- after the phrase, "in an amount".

Signed and Sealed this

Ninth Day of January, 1990

Attest:

JEFFREY M. SAMUELS

*Attesting Officer*      Acting Commissioner of Patents and Trademarks